United States Patent [19]

Heyser et al.

[11] Patent Number: 4,884,246
[45] Date of Patent: Nov. 28, 1989

[54] METHOD AND APPARATUS FOR REFLECTION MODE IMAGING

[75] Inventors: Richard C. Heyser, Tujunga; James A. Rooney, La Crescenta, both of Calif.

[73] Assignee: California Institute of Technology, Pasadena, Calif.

[21] Appl. No.: 145,104

[22] Filed: Mar. 29, 1988

Related U.S. Application Data

[63] Continuation of Ser. No. 821,001, Jan. 22, 1986, abandoned.

[51] Int. Cl.⁴ .............................................. G03B 42/06
[52] U.S. Cl. .......................................... 367/7; 367/11; 367/101
[58] Field of Search ................ 367/7, 8, 11, 101, 102, 367/110; 342/180; 73/603; 128/916, 660.04, 660.08

[56] References Cited

U.S. PATENT DOCUMENTS

| | | | |
|---|---|---|---|
| 3,466,652 | 9/1969 | Heyser | 367/101 |
| 3,969,578 | 7/1976 | Mezrich et al. | 73/603 |
| 4,052,888 | 10/1977 | Brown et al. | 73/625 |
| 4,119,938 | 10/1978 | Alais | 367/87 |
| 4,237,737 | 12/1980 | Nitadori | 367/7 |
| 4,258,574 | 3/1981 | Hildebrand et al. | 73/625 |
| 4,279,019 | 7/1981 | Heyser | 367/102 |
| 4,287,578 | 9/1981 | Heyser | 367/102 |
| 4,475,394 | 10/1984 | Takeda et al. | 73/629 |
| 4,476,874 | 10/1984 | Taenzer et al. | 73/861.25 |
| 4,543,826 | 10/1985 | Ferrari | 73/629 |

Primary Examiner—Thomas H. Tarcza
Assistant Examiner—Daniel T. Pihulic
Attorney, Agent, or Firm—Freilich, Hornbaker, Rosen & Fernandez

[57] ABSTRACT

A volume is scanned with a raster scan about a center of rotation using a transmitter/receiver at a selected range while gating a range window on the receiver with a selected range differential. The received signals are then demodulated to obtain signals representative of a property within the volume being scanned such as the density of a tumor. The range is varied until the entire volume has been scanned at all ranges to be displayed. An imaging display is synchronously scanned together with the raster scan to display variations of the property on the display. A second transmitter/receiver with associated equipment may be offset from the first and variations displayed from each of the transmitter/receivers on its separate display. The displays may then be combined stereoscopically to provide a three-dimensional image representative of variations of the property.

7 Claims, 1 Drawing Sheet

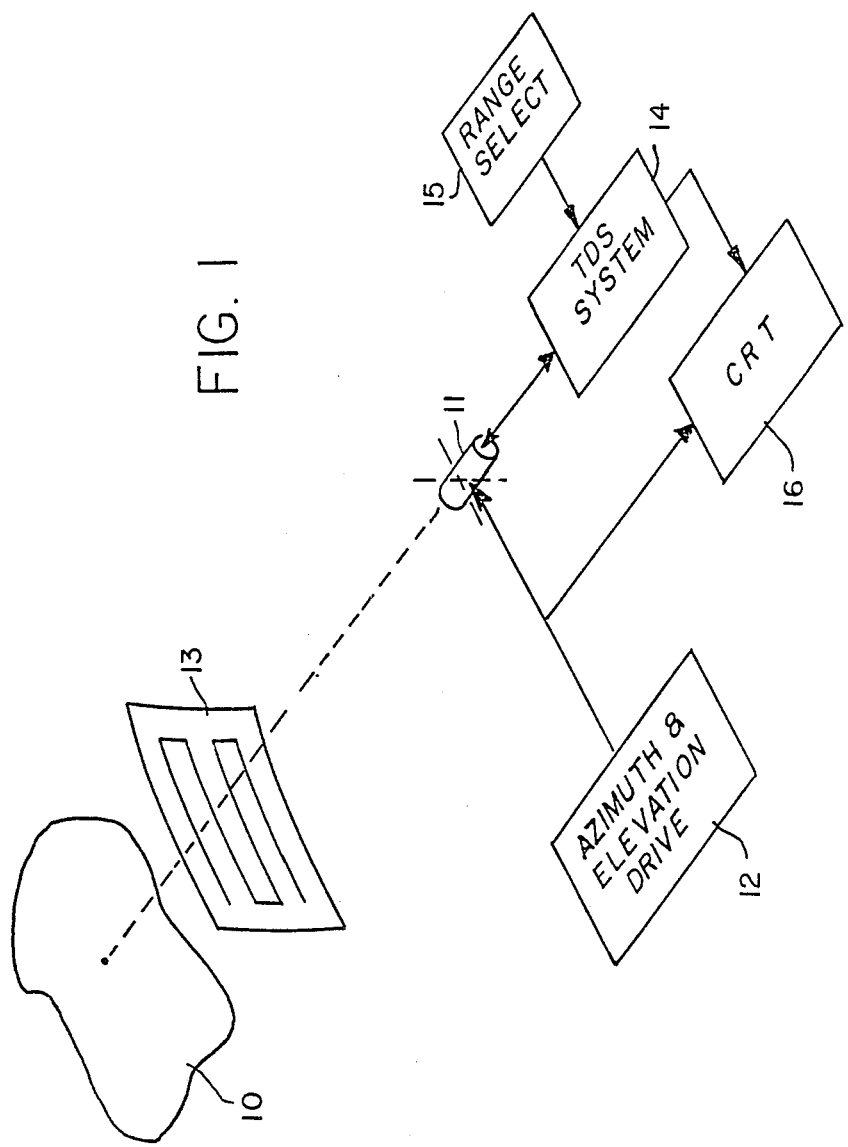

METHOD AND APPARATUS FOR REFLECTION MODE IMAGING

ORIGIN OF INVENTION

The invention described herein was made in the performance of work under a NASA contract, and is subject to the provisions of Section 305 of the National Aeronautics and Space Act of 1958, Public Law 85-568 (72 Statute 435; 482 USC 2457).

This application is a continuation of application Ser. No. 821,001, filed Jan. 22, 1986, now abandoned.

BACKGROUND OF THE INVENTION

This invention relates to a method and apparatus for reflection mode imaging and more particularly, to such method and apparatus which can display a property within a volume by taking successive cuts through the volume at selected ranges with a selected range differential, while synchronously displaying the information on a display to display variations of said property. The results of two such scanners, may be combined stereoscopically.

In the prior art, the Ledley patent 4,271,706 employs an ultrasonic scanner with a mechanical scan and gates the range of the scanning signal, using varying degrees of grey to show three dimensions. Ledley only detects surfaces and not changes in a property inside a volume and does not employ a stereoscopic effect.

Koshikawa, et al. 3,918,025, employs a different form of range gate and displays different depths by using different colors to illustrate depth. Again, only surfaces are detected and displayed, and no stereoscopic effect is employed.

Three additional prior art patents Sollish 4,028,934, Bond, et al. 4,030,342, and Uranishi 4,240,295, disclose stereoscopic recombination and raster scanning but do not employ range gating to provide accurate three-dimensional or depth information.

OBJECTS AND SUMMARY OF INVENTION

It is an object of this invention to provide a method and apparatus for reflection mode imaging of variations in a property within a volume at a selected range from a scanner with a selected range differential and synchronously displaying the variations of the property on a display.

An object of another aspect of the invention is to stereoscopically combine information from two such scanners offset to provide a three-dimensional image representative of the variations in the property.

These and other objects of the invention are achieved by scanning the volume with the raster scan about a center of rotation using a transmitter/receiver, at a selected range, while gating a range window on the receiver with a selected range differential. The received signals are then demodulated to obtain signals representative of a property within the volume being scanned. The range is varied until the entire volume has been scanned at all ranges to be displayed. An imaging display is synchronously scanned together with the raster scan to display variations of the property on the display.

In another aspect of the invention, the foregoing method and apparatus are duplicated by using a second transmitter/receiver offset from the first, each having its associated peripheral equipment as described above, displaying variations from each of the transmitter/receivers on its separate display and combining the displays stereoscopically to provide a three-dimensional image representative of variations in the property.

The novel features that are considered characteristic of this invention are set forth with particularity in the appended claims. The invention will best be understood from the following description when read in connection with the accompanying drawings.

BRIEF DESCRIPTION OF THE DRAWINGS

FIG. 1 illustrates in schematic and block diagram form an apparatus for carrying out the method of the invention.

DESCRIPTION OF THE PREFERRED EMBODIMENT

Referring to FIG. 1 an object 10 to be scanned has a volume with characteristic properties within the volume which may vary, such as a tumor within an organ in the body. The characteristics of the tumor may not present defined surfaces, but rather gradations of density or other properties. The present invention is also intended for use with targets of high curvatures, such as the eyeball, so that it can be scanned in three dimensions.

An ultrasonic transmitter/receiver 11 is employed and is driven in azimuth and elevation by azimuth and elevation drive 12 to scan the object 10 in a raster scan, such as illustrated at 13. The form of the raster used is not important. Ultrasonic transmitter/receiver 11 receives a signal from a time-delay spectrometer system 14 so that only signals at a given range are detected by the receiver. A range differential is selected by providing a range select signal for window depth to time-delay spectrometer 14 from range select subsystem 15. In this manner, transmitter/receiver 11 will look at a slice of object 10 having a range of a thickness set by the window depth provided by range select 15. CRT display 16 is synchronously driven by azimuth and elevation drive 12 together with transmitter/receiver 11. The signal received by transmitter/receiver 11 is demodulated in time-delay spectrometer 14 and fed to display 16 for synchronous display. The time-delay spectrometer 14 and CRT 16 are of the type disclosed in issued U.S. Pat. No. 4,279,019. A prior issued U.S. Pat. No. 3,466,652 also discloses apparatus of this type. Both these patents are based on inventions of R. C. Heyser, a co-inventor in this application, and are assigned to California Institute of Technology. A characteristic of the property of the volume 10, such as the density of a tumor or other object within volume 10, at the range and within the window depth employed, may be reflected by the amount or amplitude of the sound received back by transmitter/receiver 11 or by phase changes in the received sound, which information can be demodulated in time-delay spectrometer 14 and displayed on display 16 in varying shades of grey, varying colors, or any other like manner to display variations in the property.

When a radiation means, as for example an ultrasound acoustic wave, passes through a medium of propagation, there is a characteristic property of that medium called impedance. In the case of acoustic waves, impedance is expressed as the ratio of sound pressure to induced particle velocity; whereas, in the case of electromagnetic waves, impedance is expressed as the ratio of the electric to induced magnetic field. As long as the impedance is constant and independent of position, there is no reflection of wave energy. However, when the wave encounters a change in impedance, such as occurs at boundaries or wherever inhomogeneities in structure exist in the supporting medium, then a portion of the propagating energy will be reflected back toward the receiving transducer. If the change in impedance is purely resistive, such as caused by local dissipation of wave energy without energy storage at the point of reflection, then the reflected wave suffers only a change in amplitude, or amount, relative to the incident wave. On the other hand, if the change is impedance is caused by a local energy storage mechanism, such as a pure resonance in the medium, then the reflected wave will differ from the incident wave in both the amplitude and phase. It is the interception and categorization of this reflected energy which is the intent of this application, for the precise nature of the reflected wave energy relative to the forward propagating wave energy, indicates the physical or electrical state of that portion of the medium which caused the reflection to occur.

Two transmitters such as transmitter/receiver 11 may be spatially offset so as to represent the equivalent location of a left-eye view and a right-eye view, each having drives and other associated circuitry such as employed by transmitter/receiver 11 in FIG. 1. The dual representations of the scans on the two displays similar to display 16 of FIG. 1 may be viewed by stereoscopic means, providing a visual stereoscopic presentation which may be used for ease of identification of subtle features within the depth of the range window being scanned at that time.

Although a particular embodiment of the invention has been described and illustrated herein, it is recognized that modifications and variations may readily occur to those skilled in the art, such as in the characteristic of the signal being demodulated to derive the characteristic of the property within the volume at the point being scanned. Consequently, it is intended that the claims be interpreted to cover such modifications and variations.

What is claimed is:

1. A method of reflection mode imaging of a property within a volume including the steps of scanning said volume with a raster scan about a center of rotation using a transmitter/receiver, generating a signal to be transmitted using a time-delay spectrometer for sweeping the signal to be transmitted in frequency as a function of time and receiving a reflected signal modulated in amplitude and phase shift by said volume as said signal is reflected, selecting a total range differential of said frequency sweep for said transmitter as a function of time, gating a range window on said receiver with selected range differentials as a function of time for all ranges of interest at successive raster scan positions, demodulating the phase and amplitude of received signals falling within said selected range differential to obtain signals representative of a characteristic of said property while varying said range window until said volume has been scanned at all ranges and synchronously scanning an imaging display in a manner corresponding with said raster scan to display variations of said characteristics on said display at selected ranges.

2. The method of claim 1 wherein the step of demodulating the phase and amplitude of received signals is carried out using said time-delay spectrometer.

3. The method of claim 2 wherein said characteristics of said property are displayed as variations in color.

4. The method of claim 2 wherein said characteristics of said property are displayed as variations in shades of grey.

5. A method of reflection mode imaging of a property of a volume as defined in claim 12 including the further steps of offsetting two of said transmitter/receivers, each having its own time-delay spectrometer means used in the same method, displaying variations in characteristics of said property for signals received through each of said transmitter/receivers, and combining said displays stereoscopically to provide a three-dimensional image representative of said property.

6. Apparatus for reflection mode imaging of a property within a volume including a transmitter/receiver, time-delay spectrometer means for generating a signal to be transmitted into said volume, wherein said means sweeps the frequency of said signal to be transmitted as a function of time, means for selecting a total range of said frequency sweep for said transmitter as a function of time, means for gating a range window on a return signal received with a selected total range of frequency sweep as a function of time, said received signal returned from said volume being modulated in amplitude and phase, means for scanning said volume while sweeping the frequency of the transmitted signal and varying the selected range of said return signal, means for demodulating the phase and amplitude of return signals received while gating said range window to derive a signal representative of a characteristic of said property, means for displaying said demodulated signal, and means for scanning said display means synchronously with said transmitter/receiver while applying said demodulated signals to said display means to display variations of said property at selected ranges on said display means.

7. Apparatus as defined in claim 6 wherein said means for demodulating return signals received employs said time-delay spectrometer.

* * * * *